United States Patent [19]

Preiss

[11] Patent Number: 5,155,223

[45] Date of Patent: Oct. 13, 1992

[54] PREPARATION OF QUINOLINECARBOXYLIC ACIDS

[75] Inventor: Michael Preiss, Wuppertal, Fed. Rep. of Germany

[73] Assignee: Bayer Aktiengesellschaft, Leverkusen, Fed. Rep. of Germany

[21] Appl. No.: 709,531

[22] Filed: Jun. 3, 1991

[30] Foreign Application Priority Data

Jun. 14, 1990 [DE] Fed. Rep. of Germany ........ 4019023

[51] Int. Cl.$^5$ .......................................... C07D 401/04
[52] U.S. Cl. ................................................... 544/363
[58] Field of Search ......................................... 544/363

[56] References Cited

U.S. PATENT DOCUMENTS

| | | | |
|---|---|---|---|
| 4,753,925 | 6/1988 | Grohe et al. | 544/363 |
| 4,755,513 | 7/1988 | Tone et al. | 544/363 |
| 4,774,246 | 9/1988 | Chu | 544/363 |
| 4,780,468 | 10/1988 | Bridges et al. | 544/363 |
| 4,795,751 | 1/1989 | Matsumoto et al. | 544/363 |
| 4,871,852 | 10/1989 | Hayakawa et al. | 544/363 |
| 4,880,806 | 11/1989 | Ueda et al. | 544/363 |
| 4,886,810 | 12/1989 | Matsumoto et al. | 544/363 |
| 4,908,366 | 3/1990 | Schriewer et al. | 544/363 |
| 4,920,120 | 4/1990 | Domagala et al. | 544/363 |
| 4,929,613 | 5/1990 | Culbertson et al. | 544/363 |
| 4,935,512 | 6/1990 | Frank et al. | 544/363 |
| 4,971,970 | 11/1990 | Miyamoto et al. | 544/363 |
| 4,977,154 | 12/1990 | Sanchez et al. | 544/363 |
| 4,980,353 | 12/1990 | Grohe et al. | 544/363 |
| 5,013,841 | 5/1991 | Matsumoto et al. | 544/363 |

FOREIGN PATENT DOCUMENTS

| | | |
|---|---|---|
| 0140116 | 5/1985 | European Pat. Off. |
| 0178388 | 4/1986 | European Pat. Off. |
| 0226961 | 7/1987 | European Pat. Off. |
| 0247464 | 12/1987 | European Pat. Off. |
| 0264050 | 4/1988 | European Pat. Off. |

Primary Examiner—Cecilia Tsang
Attorney, Agent, or Firm—Sprung Horn Kramer & Woods

[57] ABSTRACT

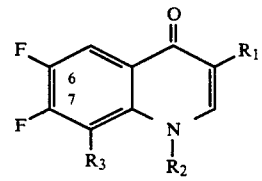

is reacted with an amine

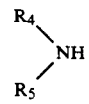

to give the compound of the formula

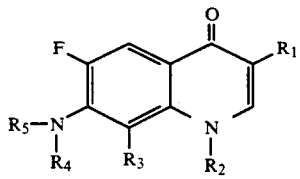

Because the starting material (I) has F in 7-position rather than Cl, the reaction proceeds at relatively low temperature with minimum side reactions.

3 Claims, No Drawings

PREPARATION OF QUINOLINECARBOXYLIC ACIDS

The invention relates to a process for the preparation of quinolinecarboxylic acids, which is characterized in that compounds of the formula (I)

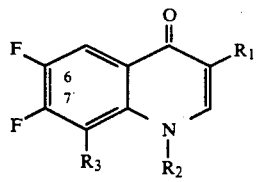

in which
$R_1$ can be COO-alkyl, cyano, CONAlk$_2$ or COOH,
$R_2$ can be substituted or unsubstituted alkyl, substituted or unsubstituted cycloalkyl, NH-alkyl, NAlk$_2$, aryl or fluorine-substituted aryl, and
$R_3$ can be alkyl, cycloalkyl, halogen, cyano, nitro, alkylthio, alkoxy, carboxyl or hydrogen, or
$R_2$ and $R_3$ can be bonded to one another by a substituted or unsubstituted alkyl chain which can be interrupted by heteroatoms,
are reacted with compounds of the formula (II)

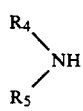

in which
$R_4$ and $R_5$ are identical or different and represent hydrogen, a branched or unbranched alkyl, alkenyl or alkynyl radical having 1 to 12 carbon atoms, which can optionally be substituted by hydroxyl groups, alkoxy, alkylmercapto or dialkyl-amino groups having 1 to 3 carbon atoms in each alkyl radical, by the nitrile group or by an alkoxycarbonyl group having 1 to 4 carbon atoms in the alcohol moiety, or represent cycloalkyl having 3 to 6 carbon atoms, or furthermore, together with the nitrogen atom which they substitute and, optionally a heteroatom such as, for example, oxygen, sulphur or NR$_6$, form a 3- to 7-membered ring which can be monosubstituted or polysubstituted by alkyl or alkenyl groups having 1 to 6 carbon atoms, hydroxyl, alkoxy or alkylmercapto groups having 1 to 3 carbon atoms, an alkoxycarbonyl group having 1 to 4 carbon atoms in the alcohol moiety, the nitrile group or also a phenyl radical, and can also contain a double bond and
$R_6$ represents hydrogen, a branched or unbranched alkyl, alkenyl or alkynyl group having 1 to 6 carbon atoms, which can optionally be substituted by hydroxyl, alkoxy, alkylmercapto and dialkylamino groups having 1 to 3 carbon atoms, an alkyl radical or the alkoxycarbonyl group having 1 to 4 carbon atoms in the alcohol moiety, a phenylalkyl group having up to 4 carbon atoms in the aliphatic moiety, which is optionally substituted in the phenyl radical, and an optionally substituted phenyl or naphthyl group or a heterocyclic radical such as, for example, a pyridine, pyrimidine, thiazole or benzothiazole ring, or also denotes an alkoxycarbonyl group having 1 to 4 carbon atoms in the alcohol moiety, which is optionally substituted by a phenyl radical, an alkanoyl radical having 1 to 6 carbon atoms, a benzoyl radical, an optionally substituted C$_1$-C$_6$-alkyl or phenylsulfphonyl radical or an optionally substituted aminosulphonyl radical, suitable substituents of phenyl and naphthyl groups being halogen, alkyl, alkoxy or alkylenemercapto groups having 1 to 3 carbon atoms, or phenyloxy, phenylmercapto, trifluoromethyl, nitro, nitrile or carboxylic ester groups having 1 to 4 carbon atoms in the alcohol moiety,
in the presence of water or mixtures of water and water-soluble solvents at temperatures of 95° to 120° C., if appropriate under pressure, to give compounds of the formula (III)

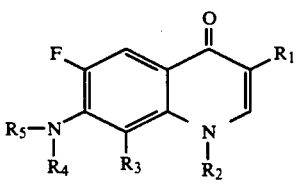

The process is preferably used for the preparation of compounds in which, in formula (I)
$R_1$ is COO-alkyl or COOH,
$R_2$ is substituted or unsubstituted alkyl, substituted or unsubstituted cycloalkyl or fluorine-substituted aryl,
$R_3$ is halogen, nitro, alkylthio, alkoxy or hydrogen,
and in formula (II)
$R_4$ and $R_5$, together with the nitrogen atom which they substitute and, if appropriate, a heteroatom such as, for example, oxygen, sulphur or NR$_6$, for a 3- to 7-membered ring which can be monosubstituted or polysubstituted by alkyl or alkenyl groups having 1 to 6 carbon atoms, hydroxyl, alkoxyl and alkylmercapto groups having 1 to 3 carbon atoms, an alkoxycarbonyl group having 1 to 4 carbon atoms in the alcohol moiety, the nitrile group and also a phenyl radical and can also contain a double bond and
$R_6$ denotes hydrogen, a branched or unbranched alkyl, alkenyl or alkynyl group having 1 to 6 carbon atoms, which can optionally be substituted by hydroxyl, alkoxy, alkylmercapto or dialkylamino groups having 1 to 3 carbon atoms, an alkyl radical, or the alkoxycarbonyl group having 1 to 4 carbon atoms in the alcohol moiety.

The process is particularly preferably used for the preparation of compounds in which, in formula (I)
$R_1$ is COO-alkyl or COOH,
$R_2$ is substituted or unsubstituted cycloalkyl,
$R_3$ is halogen or hydrogen,
and in formula (II)
$R_4$ and $R_5$, together with the nitrogen atom which they substitute and, if appropriate, a heteroatom NR$_5$, form a 5- or 6-membered ring which can be monosubstituted or polysubstituted by alkyl or alkenyl groups having 1 to 6 carbon atoms, or hydroxyl, alkoxy and alkylmercapto groups having 1 to 3 carbon atoms and can also contain a double bond and
$R_6$ denotes hydrogen, a branched or unbranched alkyl, alkenyl or alkynyl group having 1 to 6 carbon atoms, which can optionally be substituted by hydroxyl, alkoxy, alkylmercapto or dialkylamino groups having 1 to 3 carbon atoms, an alkyl radical, or the alkoxycarbonyl group having 1 to 4 carbon atoms in the alcohol moiety.

It is to be regarded as extremely surprising that the substitution of the fluorine atom takes place at an about 100 times higher rate than, for example, chlorine and bromine in the same position (position 7, formula (I)). It follows from this that the reaction already takes place at an adequate rate at temperatures around 100° C., for example in water.

A number of advantages result from the possibility of carrying out the reaction at temperatures around 100° C.:

a) On this basis as a result it is possible to work in water or aqueous mixtures, which is economical and ecologically advantageous.

b) In the preparation of compounds (III) substituted with diamines the formation of dimetric, oligomeric and polymeric by-products is strongly suppressed, as the temperature is not high enough for a condensation according to the following equation:

At the temperatures of over 140° C. customarily used, 5 mol-% and more of these products (VIII) can be formed and have to be removed in an additional process step.

Another surprising finding is the extremely high selectivity of the fluorine substitution. The fluorine atom in position 7 of the compound (I) is virtually exclusively replaced. This is shown in yields of pure (III) of around 95% of theory.

A further advantage results from the combination of the advantages mentioned, carrying out the reaction in water or water mixtures, the high selectivity and the minimum content of by-products: until now the betaine form of (III) had to be isolated in order to remove the undesired by-products (about 20%). As the latter are virtually no longer present, the isolation of the betaine form can be dispensed with especially as the subsequent reaction to give the pharmaceutically utilizable salt of

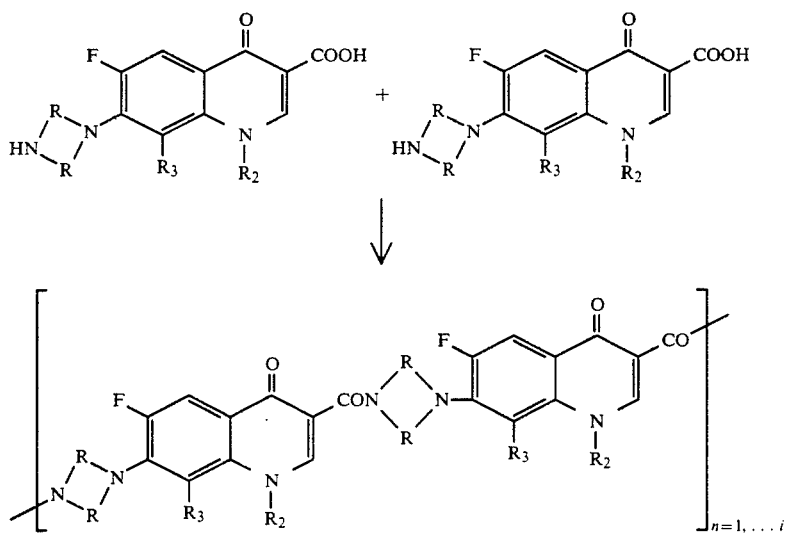

c) The formation of a further by-product is suppressed. The decarboxylated compounds (VIII) (if $R_1$=COOH) no longer occur.

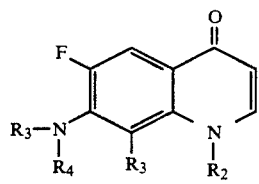

(VIII)

(III) takes place in water or water mixtures.

The reaction of compounds of the type (IV) with amines such as (II) is known in principle from EP-A-0,078,362. The selectivity of the substitution of the $C_7$-substituent (chlorine) is about 10:1 in competition with the $C_6$-substitution (fluorine); i.e. 1/10 of the valuable starting material (IV) is lost for the non-utilizable compounds (VI).

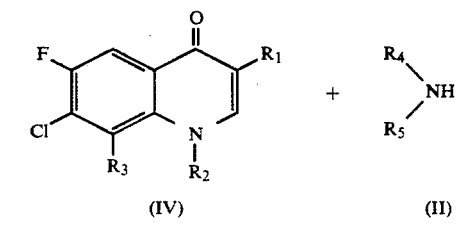

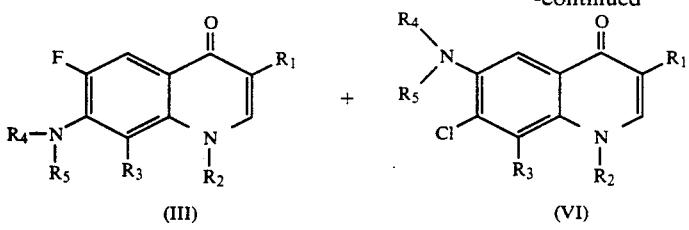

In addition, it is disadvantageous that the reaction is carried out without exception at temperatures of around 140° C. and in addition in an organic solvent.

Starting compounds of the formula (I) are disclosed in EP-A-0,169,993 and EP-A-0,274,033; however, even in this case the reaction is carried out at temperatures of 140° C. in an organic solvent, as a result of which the by-products described above have to be taken into account.

The formulation of the compounds (VI) works out disadvantageously in two ways: on the one hand, as mentioned above, 1/10 of the starting material is lost, on the other hand the separation of the compound (VI) is very difficult as its physical properties are very similar to (III) so that a certain proportion of (III) always remains in the undesired compound (VI). This loss amounts to over 10%. About 20% less of (III) is thus obtained when compounds of the type (VII) where X≠F are employed as starting materials

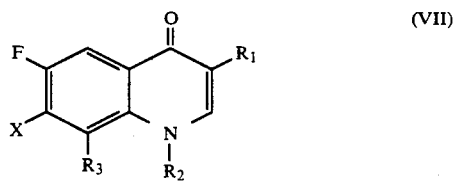

The advantages of the process according to the invention are therefore:
over 20% higher yields
virtually no by-products
water as a solvent
lower reaction temperature
saving of time as a result of omission of a process step.

The ratio of the reaction components (I) to (II) is 1:1 to 1:10, preferably 1:2 to 1:4. The reaction is preferably carried out in water as the reflux temperature which is established. However, all other water-miscible solvents which are inert under the reaction conditions used can also be employed proportionately. If desired, the reaction can also be carried out under pressure at temperatures which are above the reflux temperature. A part of the amine (II) can also be replaced by other bases, for example alkali metal hydroxide solutions or tertiary amines.

EXAMPLES

Example 1

26.5 parts by weight of 1-cyclopropyl-6,7-difluoro-1,4-dihydro-4-oxo-3-quinolinecarboxylic acid are introduced into a solution of 26.7 parts by weight of piperazine in 200 parts by volume of water, which is heated to reflux. The mixture is kept under reflux for 90 minutes and then cooled. The precipitate is separated off, washed with water and dried. 31.5 parts by weight (95.2% of theory) of 1-cyclopropyl-6-fluoro-1,4-dihydro-4-oxo-7-(1-piperazinyl)-3-quinolinecarboxylic acid are obtained.

Example 2

26.7 parts by weight of piperazine and 26.5 parts by weight of 1-cyclopropyl-6,7-difluoro-1,4-dihydro-4-oxo-3-quinolinecarboxylic acid in 200 parts by volume of water are heated to 120° C. in an autoclave for 60 minutes and the mixture is then worked up as in Example 1. 30.9 parts by weight (93.4% of theory) of 1-cyclopropyl-6-fluoro-1,4-dihydro-4-oxo-7-(1piperazinyl)-3quinolinecarboxylic acid are obtained.

Example 3

17.2 parts by weight of piperazine, 4 parts by weight of sodium hydroxide and 26.5 parts by weight of 1-cyclopropyl-6;7-difluoro-1,4-dihydro-4-oxo-3-quinolinecarboxylic acid in 200 parts by volume of water are heated under reflux for 150 minutes and the mixture is then worked up as in Example 1. 29.8 parts by weight (90.0% of theory) of 1-cyclopropyl-6-fluoro-1,4-dihydro-4-oxo-76-(1-piperazinyl)-3-quinolinecarboxylic acid are obtained.

Example 4

26.7 parts by weight of piperazine and 26.5 parts by weight of 1-cyclopropyl-6,7-difluoro-1,4-dihydro-4-oxo-3-quinolinecarboxylic acid in 200 parts by volume of water are heated under reflux for 90 minutes. The mixture is then cooled to 78° C., and 200 parts by volume of ethanol and sufficient hydrochloric acid are added until the product is dissolved. The solution is separated off from a small amount of insoluble material and cooled. The precipitate is filtered off with suction, washed with ethanol and dried. 34.7 parts by weight (89.9%) of 1-cyclopropyl-6-fluoro-1,4-dihydro-4-oxo-7-(1-piperazinyl)-4-quinolinecarboxylic acid hydrochloride monohydrates are obtained.

Example 5

26.5 parts by weight of 1-cyclopropyl-6,7-difluoro-1,4-dihydro-4-oxo-3-quinoline-carboxylic acid and 35.3 parts by weight of 1-ethyl-piperazine in 200 parts by volume of water are heated under reflux for 90 minutes, and the mixture is cooled, brought to pH 7.5 using acid and worked up. 34.0 g (94.7%) of 1-cyclopropyl-6-fluoro-1,4-dihydro-4-oxo-7-(4-ethyl-1-piperazinyl)-3-quinolinecarboxylic acid are obtained.

It will be appreciated that the instant specification is set forth by way of illustration and not limitation, and that various modifications and changes may be made without departing from the spirit and scope of the present invention.

What is claimed is:

1. A process for the preparation of a quinolinecarboxylic acid or derivative thereof which comprises reacting a compound of the formula

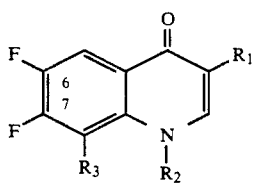 (I)

in which
  R$_1$ can be COO-alkyl or COOH,
  R$_2$ is substituted or unsubstituted alkyl, substituted or unsubstituted cycloalkyl or fluorine-substituted aryl, and
  R$_3$ is halogen, nitro, alkylthio, alkoxy or hydrogen, or
  R$_2$ and R$_3$ can be bonded to one another by a substituted or unsubstituted alkyl chain which can be interrupted by heteroatoms,
with a compound of the formula

 (II)

in which
  R$_4$ and R$_5$ together with the nitrogen atom which they substitute and optionally oxygen, sulfur or NR$_6$ form a 3- to 7-membered ring which can contain a double bond, and can be substituted by alkyl or alkenyl groups having 1 to 6 carbon atoms, hydroxyl, alkoxy or alkylmercapto groups having 1 to 3 carbon atoms, an alkoxycarbonyl group having 1 to 4 carbon atoms in the alcohol moiety, the nitrile group or a phenyl radical, and
  R$_6$ represents hydrogen, a branched or unbranched alkyl, alkenyl or alkynyl group having 1 to 6 carbon atoms, which can optionally be substituted by hydroxyl, alkoxy, alkylmercapto or dialkylamino groups having 1 to 3 carbon atoms, an alkyl radical or the alkoxycarbonyl group having 1 to 4 carbon atoms in the alcohol moiety, the optional substituents on the alkyl or cycloalkyl of R$_2$ or on the alkyl chain bonding R$_2$ to R$_3$ being inert in the reaction,
in the presence of water at a temperature from 95° to 120° C. to give a compound of the formula

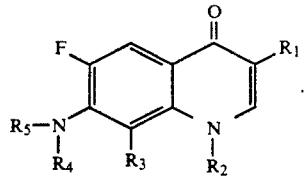 (III)

2. A process according to claim 1, in which
  R$_1$ is COO-alkyl or COOH,
  R$_2$ is substituted or unsubstituted cycloalkyl,
  R$_3$ is halogen or hydrogen,
  R$_4$ and R$_5$, together with the nitrogen atom which they substitute and optionally a heteroatom form a 5- or 6-membered ring which can be substituted by alkyl or alkenyl groups having 1 to 6 carbon atoms, hydroxyl, or alkoxy or alkylmercapto groups having 1 to 3 carbon atoms, and can also contain a double bond, and
  R$_6$ denotes hydrogen, a branched or unbranched alkyl, alkenyl or alkynyl group having 1 to 6 carbon atoms, which can optionally be substituted by hydroxyl, alkoxy, alkylmercapto or dialkylamino groups having 1 to 3 carbon atoms, an alkyl radical, or an alkoxycarbonyl group having 1 to 4 carbon atoms in the alcohol moiety.

3. A process according to claim 1, in which
  R$_1$ is COOH,
  R$_2$ is cyclopropyl,
  R$_3$ is hydrogen, and

is piperazine or 1-ethyl piperazine.

* * * * *